ized States Patent (12) United States Patent
Sofranko et al.

(10) Patent No.: US 10,138,182 B2
(45) Date of Patent: Nov. 27, 2018

(54) OXYGEN TRANSFER AGENTS FOR THE OXIDATIVE DEHYDROGENATION OF HYDROCARBONS AND SYSTEMS AND PROCESSES USING THE SAME (71) Applicants: Bio2Electric, LLC, Monmouth Junction, NJ (US); NORTH CAROLINA STATE UNIVERSITY, Raleigh, NC (US)

(72) Inventors: John A. Sofranko, Princeton, NJ (US); Fanxing Li, Cary, NC (US); Luke Neal, Cary, NC (US)

(73) Assignees: Bio2Electric, LLC, Monmouth Junction, NJ (US); North Carolina State University, Raleigh, NC (US)

( * ) Notice: Subject to any disclaimer, the term of this patent is extended or adjusted under 35 U.S.C. 154(b) by 0 days.

(21) Appl. No.: 15/514,428

(22) PCT Filed: Sep. 23, 2015

(86) PCT No.: PCT/US2015/051661
§ 371 (c)(1),
(2) Date: Mar. 24, 2017

(87) PCT Pub. No.: WO2016/049144
PCT Pub. Date: Mar. 31, 2016

(65) Prior Publication Data
US 2017/0313637 A1    Nov. 2, 2017

Related U.S. Application Data (60) Provisional application No. 62/054,424, filed on Sep. 24, 2014.

(51) Int. Cl.
C07C 5/48    (2006.01)
B01J 27/187    (2006.01)
(Continued)

(52) U.S. Cl.
CPC ............... *C07C 5/48* (2013.01); *B01J 8/0278* (2013.01); *B01J 23/002* (2013.01); *B01J 23/34* (2013.01);
(Continued)

(58) Field of Classification Search
CPC . C07C 5/48; C07C 2523/04; C07C 2527/188; C07C 2521/10; C07C 2523/34;
(Continued)

(56) References Cited

U.S. PATENT DOCUMENTS 4,443,644 A    4/1984    Jones et al.
4,443,645 A    4/1984    Jones et al.
(Continued)

FOREIGN PATENT DOCUMENTS

DE    1197871 B    8/1965
WO    WO-2013082110 A1 *    6/2013    ........... B01D 71/024

OTHER PUBLICATIONS

International Search Report and Written Opinion for International Application No. PCT/US2015/051661, dated Jan. 5, 2016—14 Pages.

Primary Examiner — Anthony J Zimmer
(74) Attorney, Agent, or Firm — RatnerPrestia (57) ABSTRACT A oxygen transfer agent useful for the oxidative dehydrogenation of saturated hydrocarbons includes at least one mixed oxide derived from manganese or compounds thereof, as well as a promoter, such as tungsten and/or phosphorus. The oxygen transfer agent may also include an alkali metal or compounds thereof, boron or compounds thereof, an oxide of an alkaline earth metal, and an oxide containing one or more of one or more of manganese, lithium, boron, and magnesium. A reactor is at least partially filled with the oxygen transfer agent in the form of a fixed or circulating bed and provides an unsaturated hydrocarbon
(Continued)

product, such as ethylene and/or propylene. The oxygen transfer agent may be regenerated using oxygen.

16 Claims, 6 Drawing Sheets

(51) Int. Cl.

| | |
|---|---|
| *B01J 35/00* | (2006.01) |
| *B01J 8/02* | (2006.01) |
| *B01J 37/04* | (2006.01) |
| *B01J 23/92* | (2006.01) |
| *B01J 27/28* | (2006.01) |
| *B01J 23/34* | (2006.01) |
| *B01J 37/00* | (2006.01) |
| *B01J 23/835* | (2006.01) |
| *B01J 23/00* | (2006.01) |
| *B01J 23/889* | (2006.01) |
| *B01J 38/12* | (2006.01) |
| *B01J 37/28* | (2006.01) |
| *B01J 37/08* | (2006.01) |
| *B01J 37/02* | (2006.01) |
| *B01J 23/94* | (2006.01) |

(52) U.S. Cl.
CPC ......... *B01J 23/835* (2013.01); *B01J 23/8892* (2013.01); *B01J 23/92* (2013.01); *B01J 27/187* (2013.01); *B01J 27/285* (2013.01); *B01J 35/002* (2013.01); *B01J 35/0006* (2013.01); *B01J 37/0036* (2013.01); *B01J 37/04* (2013.01); *B01J 37/08* (2013.01); *B01J 37/28* (2013.01); *B01J 38/12* (2013.01); *B01J 23/94* (2013.01); *B01J 35/0033* (2013.01); *B01J 37/0201* (2013.01); *B01J 2208/027* (2013.01); *B01J 2523/00* (2013.01); *C07C 2521/02* (2013.01); *C07C 2521/10* (2013.01); *C07C 2523/02* (2013.01); *C07C 2523/04* (2013.01); *C07C 2523/30* (2013.01); *C07C 2523/34* (2013.01); *C07C 2523/835* (2013.01); *C07C 2523/84* (2013.01); *C07C 2527/14* (2013.01); *C07C 2527/188* (2013.01); *Y02P 20/52* (2015.11); *Y02P 20/584* (2015.11)

(58) Field of Classification Search
CPC ............ C07C 2523/02; C07C 2521/02; C07C 2527/14; C07C 2523/84; C07C 2523/835; C07C 2523/30; B01J 27/285; B01J 23/34; B01J 27/187; B01J 35/0006; B01J 8/0278; B01J 38/12; B01J 37/08; B01J 23/92; B01J 2208/027; B01J 37/04; B01J 35/002; B01J 37/0036; B01J 23/835; B01J 23/002; B01J 23/8892; B01J 37/28; B01J 35/0033; B01J 37/0201; B01J 2523/00; B01J 23/94; Y02P 20/52; Y02P 20/584

See application file for complete search history.

(56) References Cited

U.S. PATENT DOCUMENTS

| | | | |
|---|---|---|---|
| 4,443,646 A | 4/1984 | Jones et al. | |
| 4,443,647 A | 4/1984 | Jones et al. | |
| 4,443,648 A | 4/1984 | Jones et al. | |
| 4,443,649 A | 4/1984 | Jones et al. | |
| 4,444,984 A | 4/1984 | Jones et al. | |
| 4,499,323 A | 2/1985 | Gaffney | |
| 4,499,324 A | 2/1985 | Gaffney | |
| 4,777,313 A * | 10/1988 | Sofranko | ................ B01J 21/02 585/500 |
| 2009/0234149 A1 | 9/2009 | Miyaki et al. | |
| 2012/0041246 A1 | 2/2012 | Scher et al. | |
| 2014/0275679 A1 | 9/2014 | Sofranko | |

* cited by examiner

OXYGEN TRANSFER AGENTS FOR THE OXIDATIVE DEHYDROGENATION OF HYDROCARBONS AND SYSTEMS AND PROCESSES USING THE SAME

CROSS REFERENCE TO RELATED APPLICATIONS

This is the national phase of International Application No. PCT/US2015/051661, filed 23 Sep. 2015, which claims priority to U.S. Provisional Application No. 62/054,424, filed 24 Sep. 2014. The disclosure of each of these applications is incorporated herein by reference in its entirety for all purposes.

The present application claims priority to and benefit of U.S. Provisional Patent Application No. 62/054,424, filed Sep. 24, 2014, the disclosure of which is incorporated herein by reference in its entirety for all purposes.

FIELD OF THE INVENTION

The invention relates to oxygen transfer agents and the reactor systems and processes that utilize the oxygen transfer agents for the oxidative dehydrogenation (ODH) of hydrocarbons.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of the global olefin production comes from the high temperature steam cracking of naphtha or ethane and propane. The steam cracking process, which utilizes furnaces, is highly energy intensive, and 1.5 to 2 tons of carbon dioxide is produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently centered around expanding the capacity of ethylene and propylene derived from these new sources. Numerous olefin grass root and expansion projects are either under contract or in the planning stages to take advantage of the relative low cost liquids from wet shale gas. However, there are many environmental and cost challenges to bringing on this level of new capacity.

Olefin production is the largest emitter of $CO_2$ and $NO_x$ in the organic chemical industry. With worldwide ethylene production at ~150 MT/yr, the industry emits 150-300 MT/yr of $CO_2$ and roughly 1.4 MT/yr of $NO_x$. Projects located in severe EPA non-attainment zones are challenged by the increase cost of NOx control. The total greenhouse gas (GHG) emission profile, reported in $CO_2$ equivalents, is another critical part of the permitting for all production expansions.

The industry continues to push for production technology that: (1) generates higher overall yield of ethylene and propylene; (2) increases the run length between furnace turnarounds (e.g. inspections, repairs, improvements, etc.); (3) lowers steam and energy utilization; (4) lowers all GHGs including carbon dioxide and $NO_x$. ODH of ethane and propane offers a potential solution for these needs.

The ODH of ethane and propane to olefins offers a production route that can significantly reduce $CO_2$ emissions and virtually eliminate $NO_x$ emissions from world scale plants. ODH is a selective catalytic process that produces primarily ethylene and water as products, and is thereby an exothermic reaction (reaction 1).

$$CH_3CH_3 + \tfrac{1}{2}O_2 \rightarrow CH_2CH_2 + H_2O \quad \Delta H_o = -105 \text{ kJ/mol} \quad (1)$$

The per pass yield of the ODH reaction is not limited by thermodynamic equilibrium, as it is in pyrolysis, (reaction 2).

$$CH_3CH_3 + \text{Heat} \leftrightarrows CH_2CH_2 + H_2 \quad \Delta H_o = +137 \text{ kJ/mol} \quad (2)$$

ODH provides an opportunity to achieve some of the objectives to improve the efficiency of olefin production. While a significant amount of research has been done in ODH over the last 25 years, most reported processes involve highly exothermic catalytic reactions with co-fed oxygen and hydrocarbon over platinum group metal catalysts, which are expensive materials. Therefore, there is a need for improved materials for facilitating ODH, as well as reactors and processes that include these improved materials.

SUMMARY OF THE INVENTION

In a first aspect of the present invention, an oxygen transfer agent is provided that comprises a mixed oxide having a cubic crystal lattice structure and a chemical formula of:

$$R_6R'O_8$$

wherein R is a first element, R' is a second element that is different than the first element, and O is oxygen, and the oxygen transfer agent preferably further comprises a promoter.

In a second aspect of the present invention, a reactor vessel is provided that comprises:

a reactor defining an inner volume at least partially filled with an oxygen transfer agent according to the present invention;

an inlet stream attached to the reactor, the inlet stream configured to deliver at least one of a saturated hydrocarbon and an oxygen-containing gas to the reactor; and an effluent stream attached to the reactor, the effluent stream configured to allow the removal of at least one of unsaturated hydrocarbons, water, and an oxygen-depleted gas from the reactor, wherein the reactor is configured to enable the contact of the oxygen transfer agent with at least one of the saturated hydrocarbons and the oxygen-containing gas.

In a third aspect of the invention, a process is provided comprising providing a saturated hydrocarbon to a reactor at least partially filled with an oxygen transfer agent according to the present invention, removing an effluent from the reactor containing the unsaturated hydrocarbon, and supplying oxygen to the oxygen transfer agent such that the oxygen transfer agent is oxidized.

BRIEF DESCRIPTION OF THE FIGURES

In order that the invention may be more fully understood, the following figures are provided by way of illustration, in which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

According to various embodiments of the present invention, oxygen transfer agents are provided that are useful for the ODH of hydrocarbons following the generalized formula of Equation 1:

$$zC_nH_{2n+2-2\beta}+(z-1+\delta)\text{``O''} \rightarrow C_{(z \times n)}H_{2(z \times n)+2-2\beta-2\delta}+(z-1+\delta)H_2O \quad \text{(Eq. 1.)}$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in Equation 1 may be supplied by the reduction of a metal oxide or via the catalytic use of molecular oxygen.

The oxygen transfer agents according to the present invention may also be useful for the case of Equation 1, where the carbon number, n, is equal to one. In this case the useful reaction promoted by these agents is called the oxidative coupling of methane (OCM) to higher hydrocarbons.

A few examples of the reactions described by Equation 1 that may be promoted using an oxygen transfer agent according to the present invention are shown in Table 1.

Figure 1:
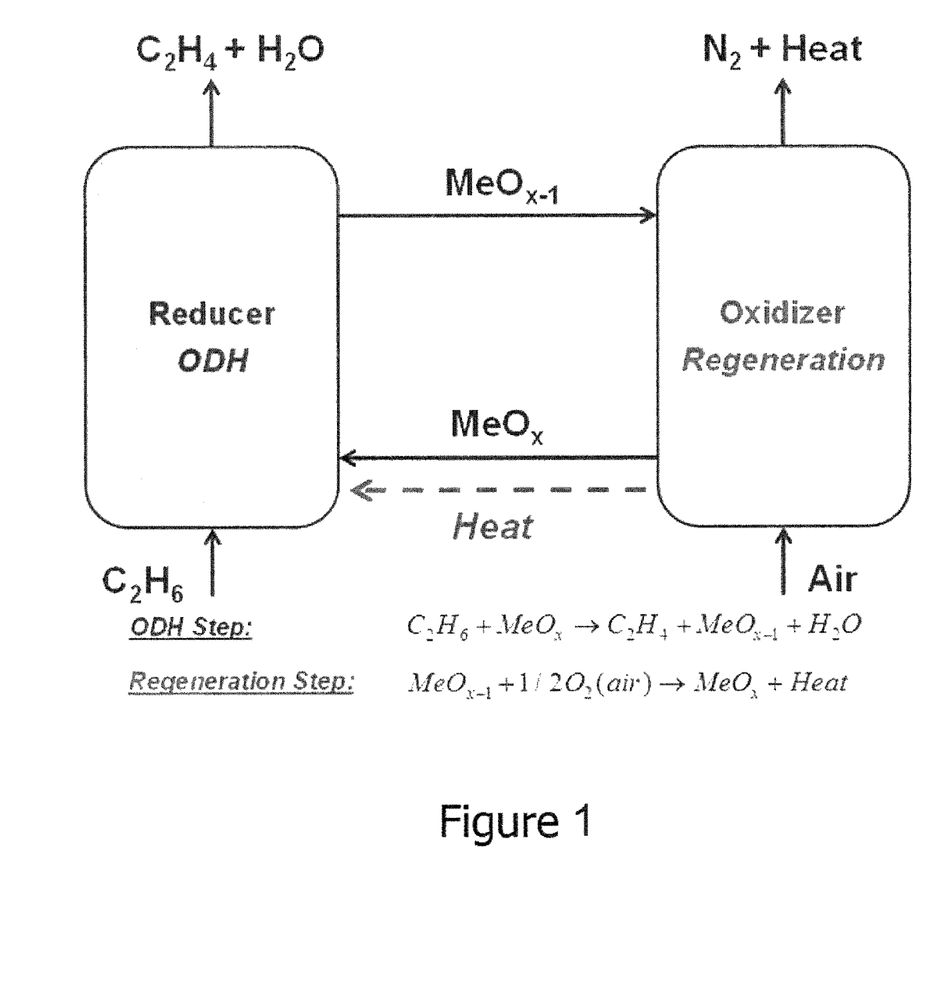
FIG. 1 is a schematic of an ODH Chemical Looping Mechanism utilizing an oxygen transfer agent according to the present invention.

While promoting the conversion of hydrocarbons according to any of the reactions of Equation 1, the oxygen transfer agent according to the present invention is reduced from an oxidized state to a less oxidized, reduced, state. In order to regenerate the agent, oxygen may be used to re-oxidize the reduced agent. This re-oxidation process may occur concurrent with the reduction of the oxygen transfer agent in the presence of one or more oxidation agent(s) such as oxygen, air, carbon dioxide, steam, NOx, and/or oxides of sulfur. A preferred embodiment of this invention is the re-oxidation of the oxygen transfer agents in a separate step. This reduction/oxidation of the oxygen transfer agent with concurrent formation of useful products, which is schematically illustrated in FIG. 1, is often described as a redox or chemical looping system.

There are many benefits of processing the ODH reaction in a chemical looping mode which include:

Ability to use inexpensive air vs. expensive oxygen via air separation equipment.

Heat balance and temperature control of reactor system via the circulation of high heat capacity solids, allowing a self-sustainable operation from an energy balance standpoint.

Ability to separate the oxidation of the hydrocarbon from the re-oxidation of the oxygen transfer agent, thereby allowing for separate reaction conditions of temperature and pressure for the two different steps.

Higher selectivity and yield to the desired products of Equation 1, with minimization of unwanted products, such as carbon oxides, than observed when the oxidation is carried out over a catalyst in a co-feed of hydrocarbon and oxygen. The presence of the oxygen transfer agent also drives the dehydrogenation equilibrium towards the product side.

Use of highly efficient, high through-put reactor systems.

Near zero emission of both carbon dioxide, sulfur oxides and nitrogen oxides.

Near zero coke accumulation on the oxygen transfer agent.

According to a first embodiment of the present invention, the oxygen transfer agent comprises an alkali metal or a compound thereof and at least one of 1) a mixed oxide of at least one metal that when contacted with a hydrocarbon is capable of oxidizing the hydrocarbon to a more unsaturated state or couples carbon-carbon bonds with the formation of water as in Equation 1; and 2) a mixed oxide of at least one metal that, when contacted with hydrogen, is capable of hydrogen oxidation.

According to a second embodiment of the present invention, the oxygen transfer agent comprises an alkali metal or a compound thereof, boron or a compound thereof, and at least one of

TABLE 1

| Starting Molecule, CnHy | Number of starting molecules = z | Cn Starting material | Degree unsaturation in starting molecule = β | Change of unsaturation in product = α | Moles of water | Moles of oxygen ("O") | Cn Product | Hn Product | Product Formula | Product Name |
| --- | --- | --- | --- | --- | --- | --- | --- | --- | --- | --- |
| CH4 | 6 | 1 | 0 | 4 | 9 | 9 | 6 | 6 | C6H6 | Benzene |
| C3H8 | 2 | 3 | 0 | 1 | 2 | 2 | 6 | 12 | C6H12 | Hexene |
| C2H6 | 2 | 2 | 0 | 2 | 3 | 3 | 4 | 6 | C4H6 | Butyne |
| CH4 | 2 | 1 | 0 | 1 | 2 | 2 | 2 | 4 | C2H4 | Ethylene |
| C4H8 | 1 | 4 | 1 | 1 | 1 | 1 | 4 | 6 | C4H6 | Butyne |
| C3H6 | 2 | 3 | 1 | 2 | 3 | 3 | 6 | 8 | C6H8 | Cyclohexadiene |
| CH4 | 2 | 1 | 0 | 0 | 1 | 1 | 2 | 6 | CH3CH3 | Ethane |

1) a mixed oxide of at least one metal that when contacted with a hydrocarbon is capable of oxidizing the hydrocarbon to a more unsaturated state or couples carbon-carbon bonds with the formation of water as in Equation 1; and 2) a mixed oxide of at least one metal that, when contacted with hydrogen, is capable of hydrogen oxidation.

According to a third embodiment of the present invention, the oxygen transfer agent comprises:

1) an alkali metal or compounds thereof,
2) boron or compounds thereof,
3) an oxide of an alkaline earth metal,
4) at least one mixed oxide derived from manganese or compounds thereof;
5) an oxide of manganese that may include Mn having a valence state selected from 4+, 3+, 8/3+, and 2+, including but not limited to $MnO_2$, $Mn_2O_3$, $Mn_3O_4$ or MnO; and
6) optionally an oxide containing one or more of one or more of manganese (Mn), lithium (Li), boron (B), and magnesium (Mg), preferably $NaB_2Mg_4Mn_2O_4$, $NaB_2Mn_2Mg_4O_{11.5}$, $Mg_6MnO_8$, $NaMn_2O_4$, $LiMn_2O_4$, $Mg_3Mn_3B_2O_{10}$, $Mg_3(BO_3)_2$, and non-crystalline compounds of these elements.

Exemplary materials that may be incorporated in various embodiments of the oxygen transfer agents of the present invention are disclosed in U.S. Pat. Nos. 4,443,649; 4,444,984; 4,443,648; 4,443,645; 4,443,647; 4,443,644; 4,443,646; 4,499,324; 4,499,323; and 4,777,313, the contents of all of which are incorporated herein by reference.

The mixed oxides included in the oxygen transfer agents useful for the present invention are prepared from materials that come from a family of cubic crystal lattice, $R_6R'O_8$, wherein R and R' are different elements and O is oxygen. These materials are solid solutions of R' in R and have been observed to show very little crystal lattice parameter change upon reduction or re-oxidation, thus making them dimensionally stable as oxygen transfer agents. Examples of materials include $Mg_6MnO_8$, $Cu_6PbO_8$ and $Ni_6MnO_8$, with $Mg_6MnO_8$ being particularly preferred.

In addition to stable crystal structures upon redox cycles, these $R_6R'O_8$ materials may be prepared in a way that yields very dense, hard, substrates. The addition of small amounts of boron greatly increases their particle toughness.

Figure 4:
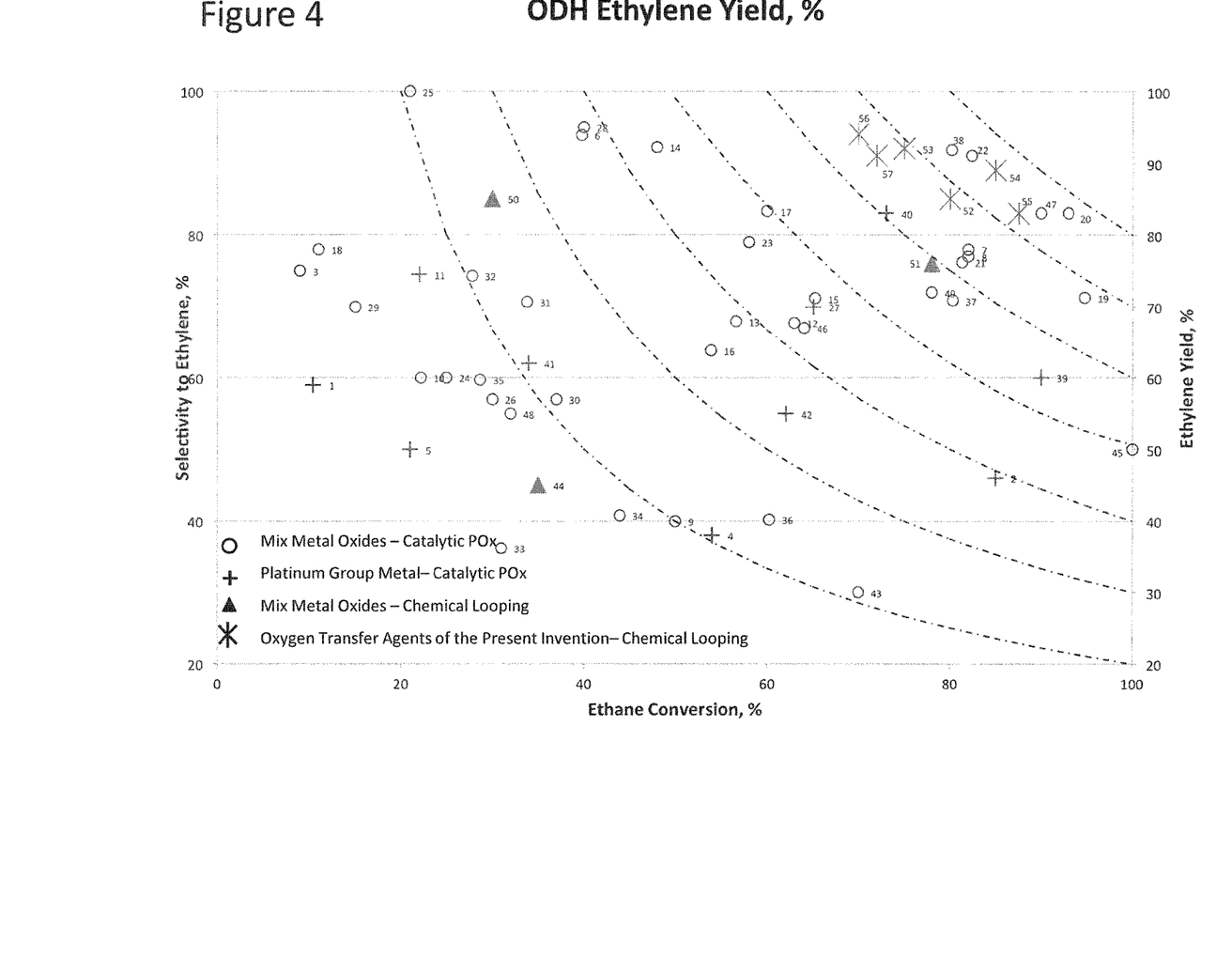
FIG. 4 is a graphical comparison of conversions, selectivities, and yields of ODH observed using oxygen transfer agents according to the present invention versus the reported conversions, selectivities, and yields of comparative catalysts.

To date, the highest reported yield via chemical looping using known catalysts is about 60%. However, the oxygen transfer agents according to various embodiments of the present invention when used to convert ethane to ethylene and higher olefins via chemical looping have exhibited yields at 70-80% (see FIG. 4).

The challenge for chemical looping, or "redox", ODH systems is to minimize the thermodynamically-favored, non-selective production of carbon dioxide. Table 2 shows thermodynamic values for pertinent reactions at 1,100 K.

TABLE 2

Relevant Thermodynamic Values

| Reaction | $\Delta H^{1,100K}$ kJ/mol* | $\Delta G^{1,100K}$ kJ/mol* |
|---|---|---|
| $CH_3CH_3 \rightarrow CH_2CH_2 + H_2$ | 143 | −4.9 |
| $CH_4 + 2\ O_2 \rightarrow CO_2 + 2\ H_2O$ | −802 | −800 |
| $CH_3CH_3 + ½\ O_2 \rightarrow CH_2CH_2 + H_2O$ | −105 | −192 |
| $CH_3CH_3 + 3½\ O_2 \rightarrow 2\ CO_2 + 3\ H_2O$ | −1429 | −1485 |
| $3\ MnO + ½\ O_2 \rightarrow Mn_3O_4$ | −223 | −99.3 |
| $H_2 + ½\ O_2 \rightarrow H_2O$ | −248 | −187 |
| $CH_3CH_3 + Mn_3O_4 \rightarrow CH_2CH_2 + H_2O + MnO$ | 118 | −92.6 |

*Values calculated using HSC Chemistry 6.0

Systems that include oxygen transfer agents according to the present invention have been found to not only exhibit higher yields of unsaturated hydrocarbons, but also exhibit reduced $CO_2$ production. The oxygen transfer agents according to the present invention promote the oxidation of hydrocarbons to more oxidized hydrocarbons in preference to the formation of carbon dioxide, carbon monoxide, or solid carbon products commonly known as coke.

The materials can promote the selective oxidation of compounds, as long as the oxygen transfer agents are at least partially oxidized, and thereby would also react with hydrogen to form water. Hydrogen may also be produced from the dehydrogenation of hydrocarbons in the reactor. As explained above, the oxygen transfer agents are reduced by the reaction with hydrogen and/or hydrocarbons in the feed stream and reoxidized by reaction with oxygen.

The oxygen transfer agents according the various embodiments of the present invention may further include a promoter that serve to promote higher selectivity to specific desired products. While not wishing to be bound to theory, it is believed that active oxygen is drawn to the promoter sites within the oxygen transfer agent. This enables the oxygen transfer agents to act as a selective promoter of Equation 1 and as an oxygen reservoir to the selective promoting agent.

Promoters that may be included in the oxygen transfer agent according to various embodiments of the present invention include, but are not limited to, 1) monometallic and mixed metallic oxides of Fe, Co, La, Sr, Sm, Pr, Y, Ga, Ce, Zr, Ti, W, Mo, V, Nb, and Cr, and
2) dopants, such as Ni, Sn, Ga, W, Zr, Na, K, Cs, Rb, As, Sb, Bi, and P.

The most preferred promoters include W and P. The oxides and dopants may co-inhibit mixed oxide structures including, but not limit to, perovskite, fluorite, bixbyite, spinel, and Ruddlesden-Popper structures.

Other promoters may include silicates or aluminates of alkaline metals or alkaline earth metals, such as silicates and aluminates of sodium, lithium, calcium, and barium. In addition, silicates and aluminates of manganese (braunite), iron, zirconium, copper or ruthenium may be used. Another class of oxygen flux promoters that may be used includes oxides with hole structures that promote oxygen anion transport such as cerium oxide, zinc oxide, zirconium oxide (with or without additives such as yttrium), praseodymium oxide, or barium oxide.

The oxygen transfer agents may be conveniently prepared by any methods known by those skilled in the art which include precipitation, co-precipitation, impregnation, granulation, spray drying, dry mixing or others. Precursors may be transformed into the active agents according to the present invention by calcination at temperatures suitable for the formation of the active components, typically in the range of 400° to 1,100° C. The calcination may be performed under any atmosphere, such as air, inert gases, hydrogen, carbon monoxide, and hydrocarbon gases, so as to form the active oxygen transfer agents of the present invention.

According to another embodiment of the present invention, a system is provided comprising a reactor containing an oxygen transfer agent useful for the ODH of hydrocarbons as described above. The system may include any reactor type known to be useful for the selective oxidation or dehydrogenation of hydrocarbons. In the instance where the conversions of Equation 1 are run in a co-feed mode with a mixture of hydrocarbon and oxidant, it will be useful to use reactors that can effectively remove the heat of reaction, such as shell and tube reactors.

The oxygen transfer agents according to various embodiments of the present invention may be used in a chemical looping system to promote an ODH reaction via a Mars-van Krevelen-like mechanism, as illustrated in FIG. 1. The effective utilization of the chemical looping mode of this invention may be performed in either fixed or circulating bed reactors. In the case of fixed bed reactors, multiple reactors may be used such that hydrocarbon oxidation and the re-oxidation of the oxygen transfer agent are occurring continuously as feed and air is alternately cycled to multiple reactors, such as the system illustrated in FIG. 2.

Figure 2:
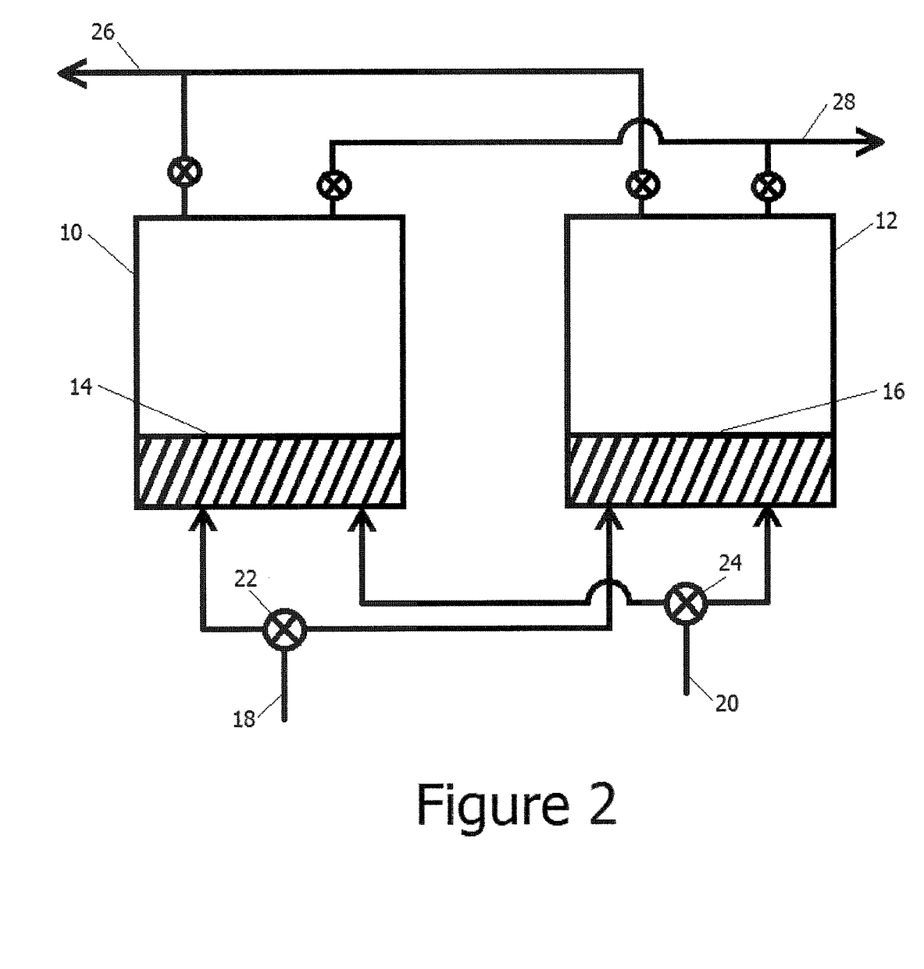
FIG. 2 is a schematic of a dual fixed bed reactor system according to one embodiment of the present invention.

In FIG. 2, two fixed-bed reactors 10, 12 each contain a layer of oxygen transfer agent 14, 16. A hydrocarbon feed line 18 for delivering a hydrocarbon, such as ethane for example, includes a valve 22 to selectively direct the hydrocarbon feed to either the first reactor 10 or the second reactor 12. If the first reactor 10 is selected, the hydrocarbon will pass through the layer of oxygen transfer agent 14, which promotes an ODH reaction, resulting in a product stream containing an unsaturated hydrocarbon, such as ethene, and water that exits the first effluent line 26. During this process in the first reactor 10, the oxygen transfer agent 14 is reduced over time. In order to regenerate the agent, the feed stream is diverted through valve 22 to the second fixed bed reactor 12, and an oxygen-containing gas stream, such as air, from feed line 20 is fed through valve 24 to the first reactor 10. The oxygen-containing gas oxidizes the oxygen transfer agent 14, and the oxygen-depleted product gas exits effluent stream 28. As the oxygen transfer agent 14 in the first reactor 10 is being regenerated through oxidation, the second reactor 12 is now producing the unsaturated hydrocarbon that exits the effluent stream 26. Upon reaching the point where regeneration of the oxygen transfer agent 16 in the second reactor 12 is necessary, the hydrocarbon feed and oxygen containing gas feeds may be switched using the valves 22, 24. This arrangement provides a continuous production of unsaturated hydrocarbon, as well as continuous oxygen transfer agent regeneration.

Figure 3:
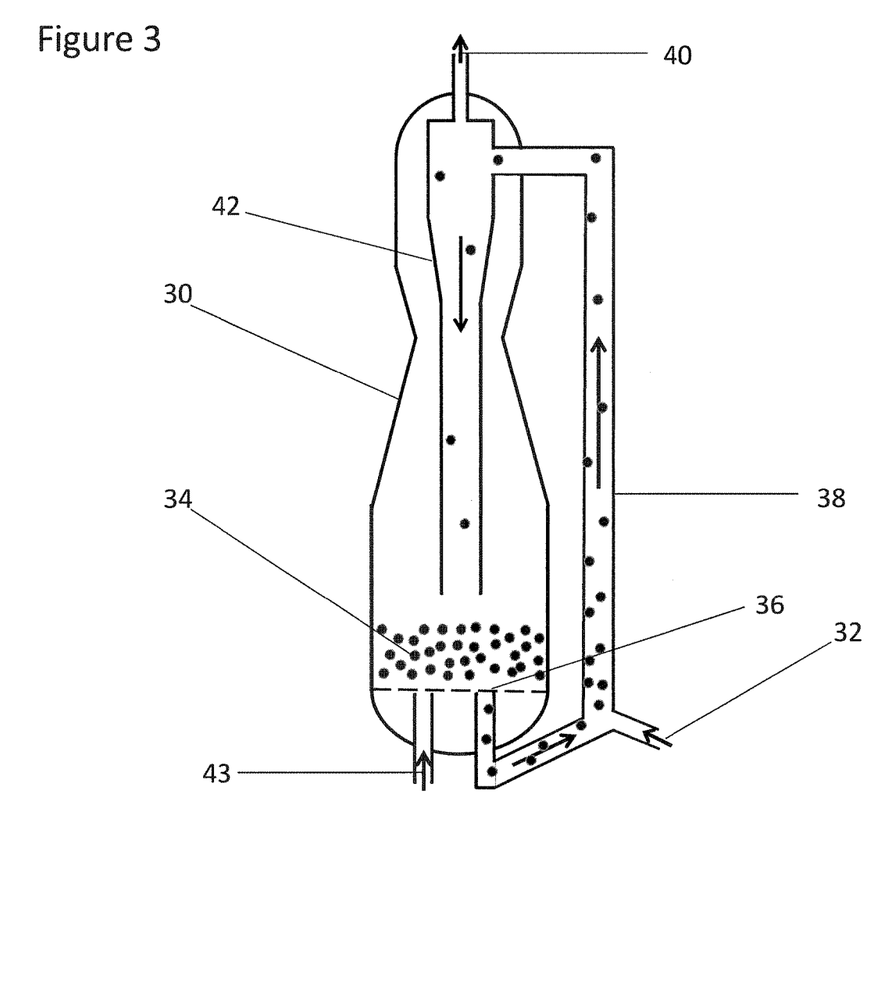
FIG. 3 is a schematic of a circulating bed reactor system according to one embodiment of the present invention.

The preferred embodiment of the current invention would be a system that includes a reactor that circulates oxygen transfer agent from a hydrocarbon reactor zone to a regeneration zone, such as the system illustrated in FIG. 3. An example of a similar reactor would be fluid catalytic cracking reactor.

In FIG. 3, a hydrocarbon feed stream 32, such as ethane, is fed to the hydrocarbon reaction section 38 of a reactor 30. Also fed to section 38 is oxygen transfer agent from bed 34 through an outlet 36 underneath the bed 34. The hydrocarbon feed and oxygen transfer agent travel together vertically through the height of the reaction section 38. As would be understood by those of skill in the art, the flow rate of reactants and dimensions of the reaction zone 38 may be optimized to maximize the reaction rate for the production of unsaturated hydrocarbons, such as ethane. The reduced oxygen transfer agent is then returned to the bed 34 via an internal return line 42, while the unsaturated hydrocarbon product exits the reactor 30 via an outlet 40. In order to regenerate the oxygen transfer agent, an oxygen-containing gas, such as air, is fed through a second inlet 43 to the bottom of the bed 34. Any oxygen-depleted gas exiting the top of the bed 34 may also exit through the outlet 40 with the product effluent.

The systems according to the present invention may be run in lean phase, dense phase particle transport, or include a free-falling bed, for example. The reactors in the systems according to various embodiments of the present invention are not limited by the fluidization regime employed in either the hydrocarbon oxidation or re-oxidation reactors.

The physical shape of the reactor is not important as long as the unit can effectively contact the reactants with the oxygen transfer agent, have effective control of the reaction contact times, have suitable mechanical stability under reaction conditions, and can be manufactured at reasonable costs.

The oxygen transfer agents according to the present invention may be porous, or dense, in so much as effective mass transport of reactants is maintained. The contact time of the feed hydrocarbons or the feed oxidant, typically air, with the oxygen transfer agent may be 0.01 seconds to 60 seconds, when calculated at reaction conditions of temperature and pressure. More typically, the contact time will be in the range of 0.1 to 20 seconds. The reaction contact times are optimized to produce the highest yield of the desired product of oxidation.

The reaction pressure in the reactors should be optimized to produce the highest yield of the desired oxidation products. Typical pressures of operation are between 0.1 and 20 atmospheres and more preferably between 1 and 15 atmospheres. The preferred temperature for reaction in the reactor is 400° to 1,000° C. A more narrow operating range of 500-950° C. may be effective depending on the type and amount of promoters included with the oxygen transfer agent. In addition, it may be beneficial to run the process at elevated pressures depending on the promoter material. The temperature and pressure should also be selected to allow for safe operation.

In yet another embodiment of the present invention, methods of using the above-described systems include the step of introducing gas phase promoters into the reactors that facilitate the desired reactions of Equation 1. The addition of gas phase promoters may greatly enhance the selectivity of the desired ODH products when used with oxygen transfer agents of the present invention. The gas phase promoters may also result in higher activity and extend the useful life of the oxygen transfer agents. Various gas phase promoters include, but are not limited to, gas phase water, steam, $CO_2$, halide gases (such as chlorine, bromine, or fluorine), hydrogen halides (such as HCl, HBr, and HF), and sulfur containing gases such as hydrogen sulfide, oxides of sulfur, and organo-sulfur compounds.

The oxygen transfer agents of the present invention may be used to convert various forms of sulfur containing natural gas which includes, but is not limited to biogas, shale gas, associated gas from oil & gas production, coal gas, or any other form of methane containing gas that also contains some form of sulfur, either organic or inorganic sulfur, to higher hydrocarbons. The oxidation of $H_2S$ contained in the natural gas into $SO_2$ and $SO_3$ has been found to be synergistically beneficial for $CO_2$ sequestration, selectivity to $C^{2+}$ products, and useful life of the oxygen transfer agent. Generally, all sulfur in the feed provided to a reactor according to an embodiment of the present invention is converted to $SO_2$, $SO_3$, or a mixture of the two sulfur gases.

Compared to current systems that utilize platinum-based materials to produce unsaturated hydrocarbons, systems according to various embodiments of the present invention advantageously generate low amounts of NOx. Systems that utilize platinum-based catalysts generally require high temperature fuel combustion or de-coking to promote the generation of unsaturated hydrocarbons. High temperatures often lead to NOx production, unless the nitrogen is removed from the feed gases used to maintain combustion in the furnaces. NOx production in these platinum-based systems may be avoided, but only by using expensive pure oxygen feed streams. The ODH reactions performed using oxygen transfer agent according to the present invention are exothermic reactions; however, the temperatures of the exotherm are relatively low compared to furnace temperatures and therefore, generate little NOx. Thus, systems and methods according to the present invention offer more environmentally friendly and less expensive alternatives to present day processes.

The effluent produced by the reactor of the present invention may comprise unconverted hydrocarbons as well as some lower value products, such as carbon dioxide and carbon monoxide that may also be formed at low concentrations. Additional components of the effluent may include oxygenated hydrocarbons, such as alcohols, which are formed in preference to the production of carbon monoxide or carbon dioxide, resulting in an effluent from the reactor with a higher molar concentration of oxygenated hydrocarbons than carbon monoxide or carbon dioxide. It is within the scope of the present invention to recycle the effluent. Similarly, lower value products, such as carbon oxides and water, may be removed from the effluent prior to further treatment.

Preferably, further downstream processes include separation methods in order to isolate polymer grade olefins. For example, ethylene fractionation may include one or more driers in order to remove water prior to feeding the dried product to a distillation column. The distillation column preferably includes several stages to provide a highly pure polymer grade ethylene product. The polymer grade olefins may then be sold as raw materials for the production of higher molecular weight products by oligomerization.

Numerous catalysts and processes are known for the oligomerization of olefins generally, and of ethylene particularly, all of which may be employed for converting the polymer grade olefins made according to the various methods of the present invention to higher molecular weight products. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like. Higher hydrocarbon products of interest may include aviation fuels, kerosene, or intermediate refining streams.

Without intending to limit the scope of the claimed invention, most oligomerization catalysts may be classified in one of two general categories: metal catalysts and acid catalysts. They may also be classified as heterogeneous (solid) catalysts or homogeneous (liquid-phase) catalysts. Examples of metal catalysts that may be used in a process according to the present invention for oligomerization of unsaturated hydrocarbons, include nickel (note that these catalysts require a donor ligand and a Lewis acid), palladium, chromium, cobalt, titanium, tungsten, and rhenium. Examples of acid catalysts include phosphoric acid and acid catalysts based on alumina.

Other acid catalysts that may be used in the present invention are silaceous, crystalline molecular sieves. Such silica-containing crystalline materials include materials which contain, in addition to silica, significant amounts of alumina, and generally known as "zeolites", i.e., crystalline aluminosilicates. Silica-containing crystalline materials also include essentially aluminum-free silicates. These crystalline materials are exemplified by crystalline silica polymorphs (e.g., silicalite and organosilicates), chromia silicates (e.g., CZM), ferrosilicates and galliosilicates, and borosilicates. Crystalline aluminosilicate zeolites are best exemplified by ZSM-5, ZSM-11, ZSM-12, ZSM-21, ZSM-38, ZSM-23, and ZSM-35.

Metal oligomerization catalysts in general are more sensitive to feed impurities, (e.g., water, carbon monoxide, dienes, etc.) than are the acid catalysts. Although homogeneous, metal catalysts are quite active, the need for dry feeds, solvents, and other measures to prevent catalyst deactivation and precipitation is disadvantageous and suggests an obvious advantage to supported, heterogeneous, metal catalyst.

Homogeneous acid catalysts are effective but, are also corrosive and tend to form two liquid-phase systems with the non-polar hydrocarbon oligomerization products. Considering the foregoing observations, heterogeneous acid catalysts are the preferred catalyst for use in the oligomerization step of the process according to the present invention. Of the heterogeneous acid catalysts, acid zeolites are especially preferred, particularly zeolites of the ZSM-type and borosilicates.

EXAMPLES

In order that the invention may be more fully understood, the following Examples are provided by way of illustration only.

Example 1

The following is an evaluation and comparison of catalysts used for the oxidative coupling of methane (OCM) and an oxygen transfer agent of the present invention when the materials are used for ethane conversion.

Ethane was fed at 4,500 $hr^{-1}$ GHSV, 850° C., through four 0.5 mL beds in a quartz U-tube reactor. Each bed contained a different material. The effluent from the bed was connected directly to a mass spectrometer, and the reaction continuously monitored over an 8 second pulse of 80% ethane. Ethane pulses were followed by a nitrogen purge and air regeneration to simulate redox cycles.

The material of Bed A was a low surface area alpha alumina inert support. The material of Bed B was a 15% manganese on magnesia. The material of Bed C was a first oxygen transfer agent according to the present invention comprising Li/Mn/B/MgO. The material of Bed D was a second oxygen transfer agent according to the present invention comprising W/P/Li/Mn/B/MgO.

The material in Bed C was prepared by ball milling manganese dioxide (32.2 grams), boric acid (11.3 grams), magnesia (42.3 grams) and lithium hydroxide (4.5 grams) with water. The milled mixture was calcined in air at 900° C. for 8 hours.

The material used in Bed D was prepared by ball milling manganese dioxide (32.2 grams), boric acid (11.3 grams), magnesia (42.3 grams) and lithium hydroxide (4.5 grams). The milled mixture was calcined in air at 900° C. for 8 hours. The resulting material was treated with phosphotungstic acid via incipient wetness technique to yield 5% W and calcined again at 900° C. for 8 hours.

Figure 5A:
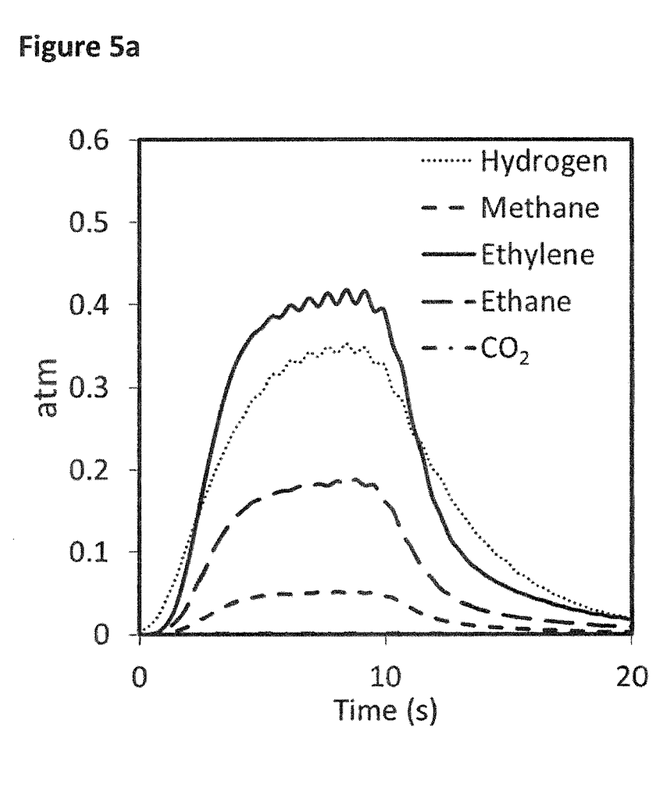
FIG. 5a is an ethane conversion profile of the reaction described in Example 1 through catalyst Bed A.
Figure 5B:
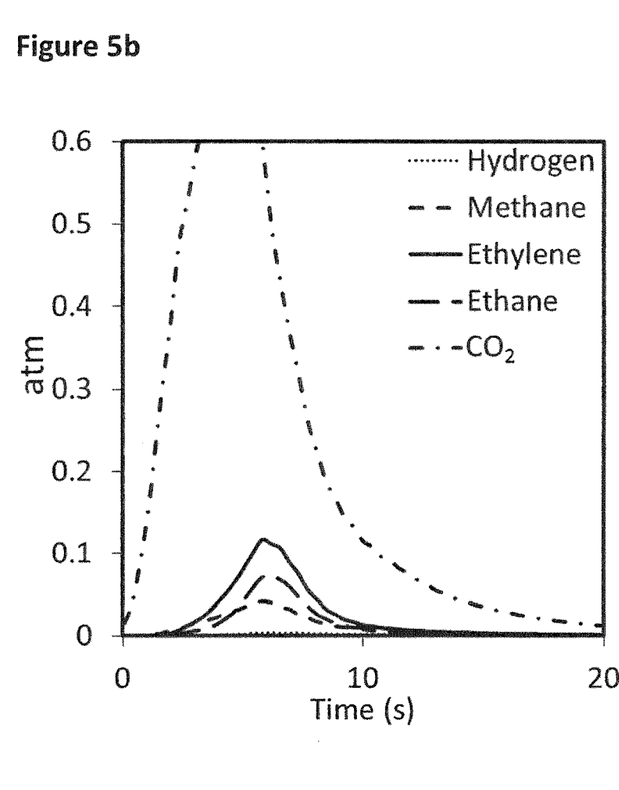
FIG. 5b is an ethane conversion profile of the reaction described in Example 1 through catalyst Bed B.
Figure 5C:
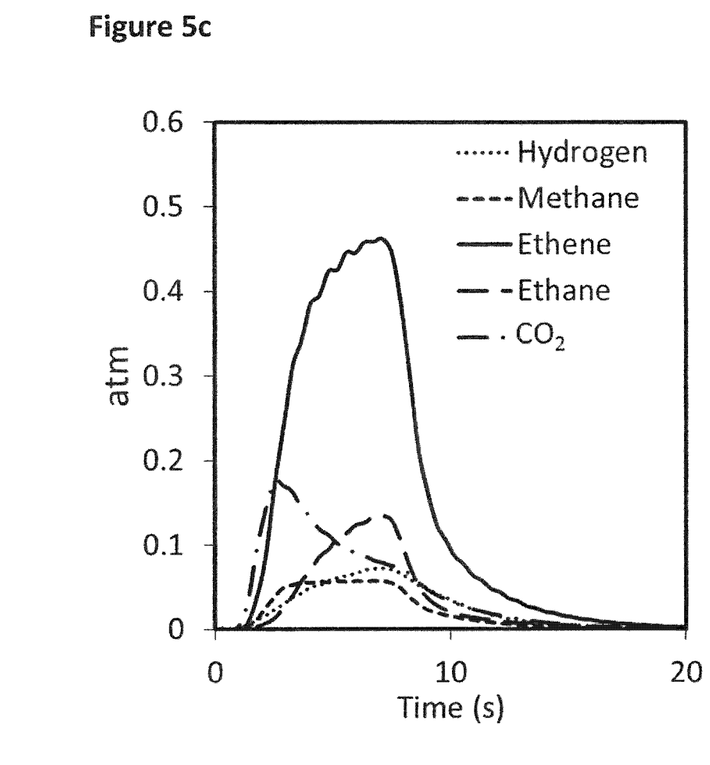
FIG. 5c is an ethane conversion profile of the reaction described in Example 1 through catalyst Bed C.
Figure 5D:
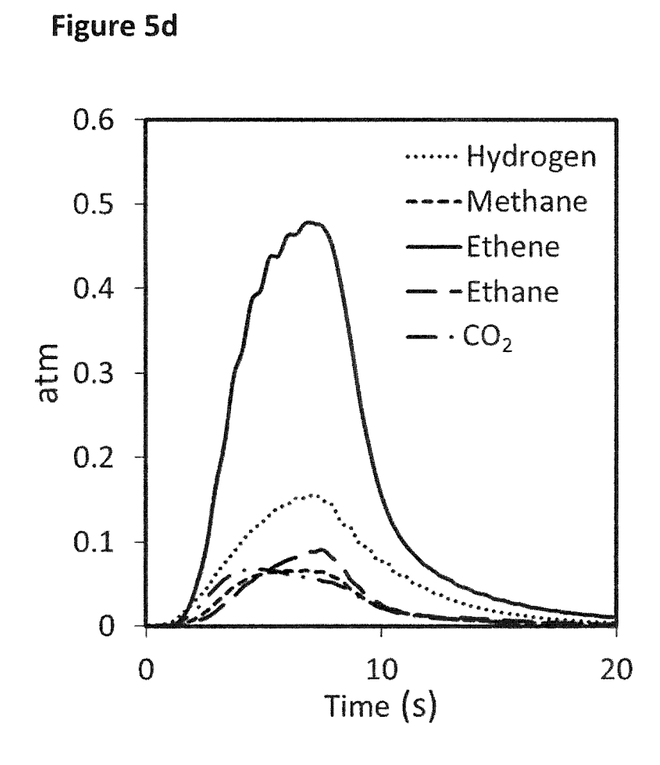
FIG. 5d is an ethane conversion profile of the reaction described in Example 1 through Bed D containing an oxygen transfer agent according to an embodiment of the present invention.

The ethane reaction profile of each of Beds A-D is provided in FIGS. 5a to 5d, respectively. Significant background thermal conversion was observed with ethylene and hydrogen as the main products, along with small traces of C3+ hydrocarbons, obtained from Bed A (FIG. 5a). In contrast, the manganese oxide catalyst supported on magnesia of Bed B consumed most product hydrogen, but was very active for the production of COx with ethylene as a minor product (FIG. 5b). The highest yields yet reported for a chemical looping ODH system were observed in FIGS. 5c and 5d using an oxygen transfer agent according to the present invention. The inclusion of W and P promoters in the oxygen transfer agent in Bed D resulted in both improved yield and selectivity over the oxygen transfer agent of Bed C.

The data demonstrates that oxygen transfer agents according to the present invention provide high C2+ olefin selectivity and that the use of a promoter is particularly advantageous. This suggests that simply changing the composition of the oxygen transfer agent enables adjustment of the amount of hydrocarbon production, thereby allowing the tuning of hydrocarbon yields based on the market needs of each specific ODH installation.

Example 2

To determine the effect of various promoters on oxygen transfer agent according to the present invention various ethane conversions were performed in a temperature range of 825-850° C. and at atmospheric pressure. The cumulative yields of the first 15 seconds of ethane conversions are provided in Table 3.

commercial scale reactor. The projections suggest that one or two large circulating bed units consisting of one ODH reactor and one regeneration unit could convert all the gas feed for a 1,000 kT/a ethylene plant. This process intensity is consistent with typical modern FCC units.

For a single, two reactor unit, a capital estimate and process economics were developed for an ODH system using an oxygen transfer agent according to the present invention. The results are provided in Table 4. The downstream recovery sections were approximated to be similar to conventional steam cracking. However, heat recovery and compression systems were factored relative to steam cracking to match the reduced load of the ODH system. In addition, the steam cracking and ODH systems were compared to an estimate for a catalytic partial oxidation route (POx).

TABLE 4

Capital and Production Cost Estimates
Comparative Ethylene Cost of
Production - Steam Cracking, POx and ODH

| Capacity: 2,147 Bil. lb./yr. 974 kT/yr. 2013 $'s | Steam Cracking | POx | ODH Base Catalyst | Advanced ODH Catalyst |
|---|---|---|---|---|
| Total Capital Investment, $ MM | 1028 | 879 | 923 | 823 |
|  | $/lb. | $/lb. | $/lb. | $/lb. |
| TOTAL CASH COST | 0.130 | 0.168 | 0.107 | 0.097 |
| Depreciation | 0.039 | 0.033 | 0.037 | 0.030 |
| 10% ROI | 0.048 | 0.041 | 0.046 | 0.038 |
| TOTAL COST OF PRODUCTION | 0.217 | 0.242 | 0.190 | 0.166 |

While the direct POx process has the potential for lower overall capital costs, pure oxygen is required for the catalytic reaction. The cost of oxygen adds about 1-2 ¢/lb. to the cost of ethylene. Using the ODH technology, one large scale fluid bed reactor may be able to convert the same ethane feed rate

TABLE 3

| Parameters | Catalyst | Li/Mn/B/MgO (No Promoters) | | | | W/P/Li/Mn/B/MgO | | | |
|---|---|---|---|---|---|---|---|---|---|
|  | Temp., ° C. | 825 | 825 | 840 | 840 | 825 | 825 | 840 | 840 |
|  | GHSV, hr$^{-1}$ | 2,400 | 4,800 | 2,400 | 4,800 | 2,400 | 4,800 | 2,400 | 4,800 |
| % Selectivity | Methane | 8.13% | 5.79% | 9.26% | 6.99% | 6.65% | 4.67% | 7.44% | 5.56% |
|  | Ethylene | 64.51% | 77.16% | 62.44% | 71.58% | 66.46% | 77.21% | 61.26% | 75.08% |
|  | Acetylene | 1.10% | 0.68% | 1.34% | 1.00% | 1.21% | 0.73% | 1.58% | 0.94% |
|  | Propylene | 2.38% | 2.53% | 2.33% | 2.50% | 2.75% | 2.49% | 2.55% | 2.55% |
|  | Propadiene | 0.06% | 0.05% | 0.07% | 0.06% | 0.07% | 0.05% | 0.09% | 0.06% |
|  | Propane | 0.43% | 0.56% | 0.36% | 0.52% | 0.41% | 0.49% | 0.30% | 0.45% |
|  | C4's | 6.29% | 6.40% | 6.24% | 6.82% | 7.79% | 7.37% | 7.55% | 7.63% |
|  | C5's | 1.63% | 1.73% | 1.63% | 2.04% | 2.22% | 2.30% | 2.19% | 2.51% |
|  | C6+'s | 2.30% | 1.33% | 2.45% | 2.45% | 2.87% | 2.04% | 3.60% | 2.21% |
|  | Coke | TR | TR | TR | TR | TR | TR | TR | TR |
| % Conversion | Ethane | 86.65% | 69.48% | 89.59% | 78.57% | 86.84% | 70.19% | 91.32% | 76.41% |
| % Selectivity | $C_2^+$ | 78.70% | 90.43% | 76.85% | 86.97% | 83.76% | 92.68% | 79.10% | 91.43% |
| % Yield | $C_2^+$ | 68.20% | 62.84% | 68.85% | 68.33% | 72.74% | 65.05% | 72.24% | 69.86% |
| % Selectivity | Carbon Dioxide | 9.86% | 2.57% | 10.30% | 4.14% | 5.74% | 1.45% | 8.19% | 1.70% |
|  | Carbon Monoxide | 3.31% | 1.20% | 3.60% | 1.89% | 3.84% | 1.21% | 5.27% | 1.31% |
| % Yield | Carbon Dioxide | 8.54% | 1.79% | 9.23% | 3.25% | 4.99% | 1.02% | 7.48% | 1.30% |
|  | Carbon Monoxide | 2.87% | 0.84% | 3.22% | 1.49% | 3.34% | 0.85% | 4.82% | 1.00% |
| % Selectivity | % $H_2$ Selectivity | 13.07% | 23.72% | 10.62% | 19.11% | 4.18% | 9.13% | 6.61% | 9.00% |
|  | % $H_2O$ Selectivity | 86.93% | 76.28% | 89.38% | 80.89% | 95.82% | 90.87% | 93.39% | 91.00% |

Example 3

Product profiles interpolated from example 2 were incorporated into standard industrial process simulation software. The simulation was used to project the productivity of a as 6-8 steam cracking furnaces. This will save on capital and reduce the turnaround schedule for the plant. A steam cracker requires multiple turnarounds each year. In comparison, an FCC unit may go 2-3 years before a turnaround, as the circulating material is continuously regenerated and replenished. The same extended turnaround schedule for the ODH process is expected.

One of the biggest benefits of ODH is the more than 90% reduction in production of $CO_2$. The exothermic ODH reaction generates excess heat that is used for downstream processing. In addition, since no high temperature furnace is required, NOx production will be extremely low. These environmental benefits may not only save capital and lower operating costs, but they may allow for a quicker permitting process.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed:

1. An oxygen transfer agent for the oxidative dehydrogenation of unsaturated hydrocarbons, said oxygen transfer agent comprising:
   a mixed oxide which is $Mg_6MnO_8$, and
   at least two promoters which include W and P.

2. The oxygen transfer agent of claim 1 further comprising an alkali metal or compounds thereof.

3. The oxygen transfer agent of claim 2 further comprising boron or compounds thereof.

4. The oxygen transfer agent of claim 3 further comprising an oxide of an alkaline earth metal.

5. The oxygen transfer agent claim 1 further comprising an oxide of manganese, wherein the manganese has a valence state selected from 4+, 3+, 8/3+, and 2+.

6. The oxygen transfer agent of claim 1 further comprising at least one of $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and a non-crystalline compound comprising oxygen and at least one of sodium, boron, magnesium, manganese, and lithium.

7. A system for the oxidative dehydrogenation of unsaturated hydrocarbons comprising:
   a reactor defining an inner volume at least partially filled with an oxygen transfer agent according to claim 1;
   an inlet stream attached to the reactor, the inlet stream configured to deliver at least one of a saturated hydrocarbon and an oxygen-containing gas to the reactor; and
   an effluent stream attached to the reactor, the effluent stream configured to allow the removal of at least one of unsaturated hydrocarbons, water, and an oxygen-depleted gas from the reactor,
   wherein the reactor is configured to enable the contact of the oxygen transfer agent according to claim 1 with at least one of the saturated hydrocarbons and the oxygen-containing gas.

8. The system of claim 7 further comprising a source of unsaturated hydrocarbon attached to the inlet stream.

9. The system of claim 7 further comprising a source of oxygen-containing gas attached to the inlet stream.

10. The system of claim 9 wherein the oxygen-containing gas is air.

11. The system of claim 7 wherein the reactor further comprises a hydrocarbon reaction section configured to circulate the oxygen transfer agent within the inner volume of the reactor.

12. A process for the production of an unsaturated hydrocarbon comprising:
   providing a saturated hydrocarbon to a reactor at least partially filled with an oxygen transfer agent according to claim 1;
   contacting the saturated hydrocarbon with the oxygen transfer agent to convert the saturated hydrocarbon into the unsaturated hydrocarbon;
   removing an effluent from the reactor containing the unsaturated hydrocarbon; and
   supplying oxygen to the oxygen transfer agent such that the oxygen transfer agent is oxidized.

13. The process of claim 12, wherein the supplying of the oxygen is performed intermittently between periods of providing the saturated hydrocarbon.

14. The process of claim 12 further comprising separating the unsaturated hydrocarbon from the effluent.

15. The process of claim 12 wherein the saturated hydrocarbon is at least one of ethane and propane.

16. The process of claim 12 wherein the unsaturated hydrocarbon is at least one of ethylene and propylene.

* * * * *

UNITED STATES PATENT AND TRADEMARK OFFICE
CERTIFICATE OF CORRECTION

PATENT NO. : 10,138,182 B2
APPLICATION NO. : 15/514428
DATED : November 27, 2018
INVENTOR(S) : John A. Sofranko, Fanxing Li and Luke Neal It is certified that error appears in the above-identified patent and that said Letters Patent is hereby corrected as shown below:

In the Specification

At Column 1, beginning at Line 20, please add the following:
STATEMENT REGARDING FEDERALLY SPONSORED RESEARCH
This invention was made with government support under grant number DE-AR0000327 awarded by the Department of Energy. The government has certain rights in the invention.

Signed and Sealed this
Third Day of November, 2020

Andrei Iancu
*Director of the United States Patent and Trademark Office*